United States Patent [19]

Iannuzzelli et al.

[11] Patent Number: 4,529,003
[45] Date of Patent: Jul. 16, 1985

[54] MANIFOLD

[75] Inventors: Vincent F. Iannuzzelli, Califon, N.J.; Carl P. Kremer, Jr., Darien, Conn.

[73] Assignee: Syntex, Inc., Palo Alto, Calif.

[21] Appl. No.: 477,276

[22] Filed: Mar. 21, 1983

[51] Int. Cl.³ .............................................. F16K 17/18
[52] U.S. Cl. ................................. 137/493.8; 128/1.1; 128/200.14; 137/512; 137/DIG. 9
[58] Field of Search .............. 137/512, DIG. 9, 493.8; 128/1.1, 200.14, 200.16, 203.28

[56] References Cited

U.S. PATENT DOCUMENTS

| | | | |
|---|---|---|---|
| 1,509,810 | 9/1924 | MacIndoe | 137/493.8 X |
| 2,955,843 | 10/1960 | Chuba | 137/493.8 X |
| 3,695,254 | 10/1972 | Blum | 128/1.1 X |
| 3,945,378 | 3/1976 | Paluch | 128/200.18 X |
| 4,195,552 | 4/1980 | Neff | 137/493.8 X |

FOREIGN PATENT DOCUMENTS

| | | | |
|---|---|---|---|
| 1091265 | 10/1954 | France | 137/493.8 |
| 577645 | 5/1946 | United Kingdom | 128/203.28 |

Primary Examiner—Robert G. Nilson
Attorney, Agent, or Firm—Bernard, Rothwell & Brown

[57] ABSTRACT

A manifold is described, for delivery of radioaerosol to a patient, having a pair of rigid conduits joined at one end to form a first connector and at the other end to form a second connector. A third connector is formed in the first conduit between the first and second connectors and a one way-valve is located between the first and third connector. A second one-way valve is located in the second conduit to permit exhalation by the patient.

4 Claims, 12 Drawing Figures

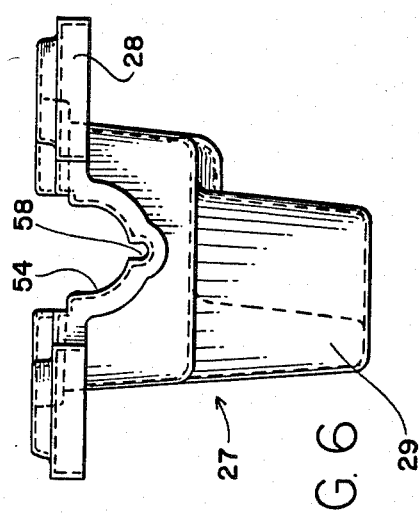
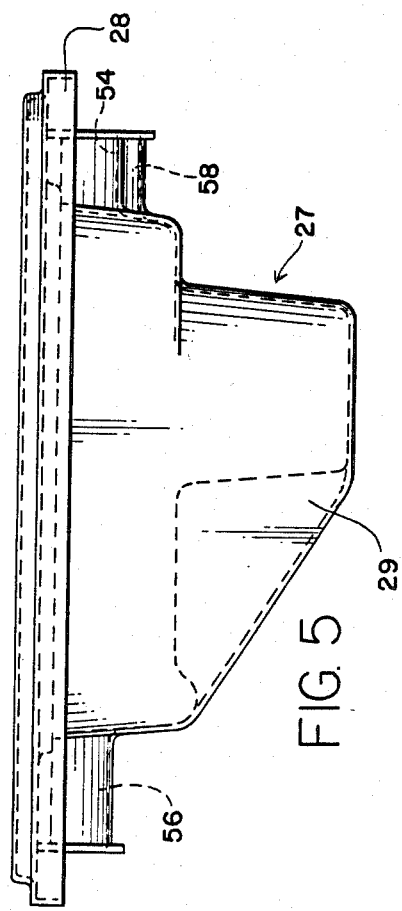
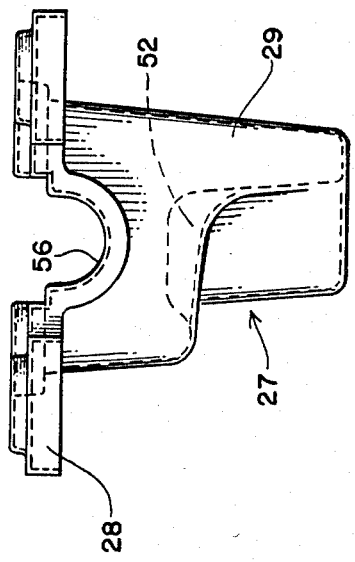

MANIFOLD

BACKGROUND OF THE INVENTION

1. Field of the Invention

This invention relates to flow distribution apparatus for radioactive aerosols. In particular, the invention relates to a manifold utilized with radioaerosol delivery systems in nuclear medicine.

2. State of the Art

Lung ventilation scanning using radiolabled aerosols has been studied for about the last 20 years. However, until recently when improved aerosol generating devices have become more generally available, practical applications of such methods have been extremely limited. One particularly useful aerosol generating system is that described in U.S. Pat. No. 4,116,387 and U.S. Pat. No. 4,251,033, the disclosures of which are incorporated herein by reference. The nebulizer described in those patents has been found to be particularly useful in generating aerosols having a particle size and particle size distribution to make lung scanning a useful diagnostic tool. Relatively recent articles describing lung scanning methodology utilizing radioactive aerosols can be found at: *Radiology*, 131:256-258, April 1979; *Seminars in Nuclear Medicine*, Volume X, No. 3 (July), 1980, pp. 243-251; and *The Journal of Nuclear Biology and Medicine*, Vol. 19, No. 2, 1975, pp. 112-120.

Because of the increased interest in using radioaerosols for diagnostic imaging, there is a need for a compact and practical apparatus for delivering such radioaerosols to a patient. The invention described herein is considered to satisfy such a need.

SUMMARY OF THE INVENTION

The invention is directed to a manifold comprising a first, rigid conduit and a second, rigid conduit joined at one end to form a first connector and at the other end to form a second connector; a third connector located in the first conduit between the first and second connector; a first, one-way valve located in the first conduit between the first connector and the third connector permitting fluid flow through the first conduit in a direction from the first connector toward the second connector; and a second, one-way valve located in the second conduit permitting fluid flow through the second conduit in a direction from the second connector toward the first connector and preventing flow in the reverse direction. In a presently preferred embodiment the two conduits define an opening between them and have an attachment means formed thereon to attach the manifold to a manifold support means. Additionally, the third connector on the manifold is provided with a locking groove to engage a complementary ring in the mouth of a nebulizer.

DETAILED DESCRIPTION OF THE DRAWINGS

FIG. 5 is a side view of the inner shell;

FIG. 6 is a view of one end the inner shell of FIG. 5;

FIG. 7 is a view of the other end of the inner shell of FIG. 5;

DETAILED DESCRIPTION OF THE INVENTION

Figure 1:
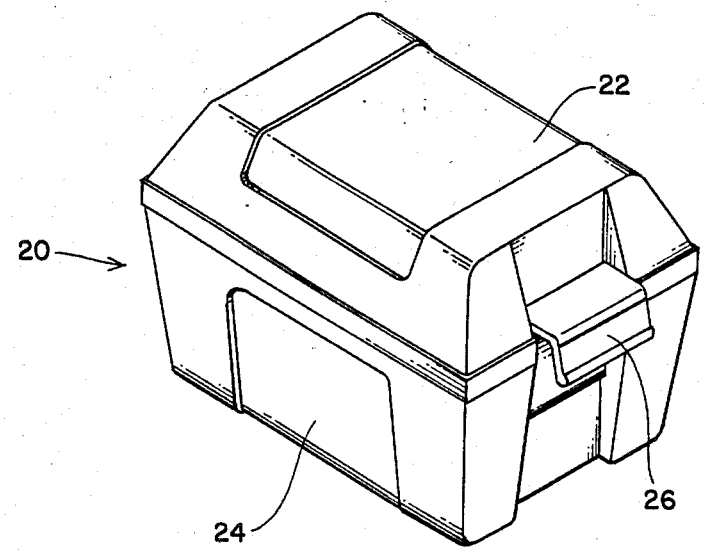
FIG. 1 is a perspective view of a shielding container.

The manifold 88 of this invention, which will be described more fully below, is particularly useful with the shielding apparatus and container 20 illustrated generally in FIG. 1. Container 20 has an outer shell 24 upon which is located a closure lid 22. Lid 22 is hingedly connected to outer shell 24 and can be secured to outer shell 24 by handle members 26 (one of which is illustrated) which are also hingedly connected to the outer shell 24. The members 26 function both as handles and as a closure means for the container.

Figure 2:
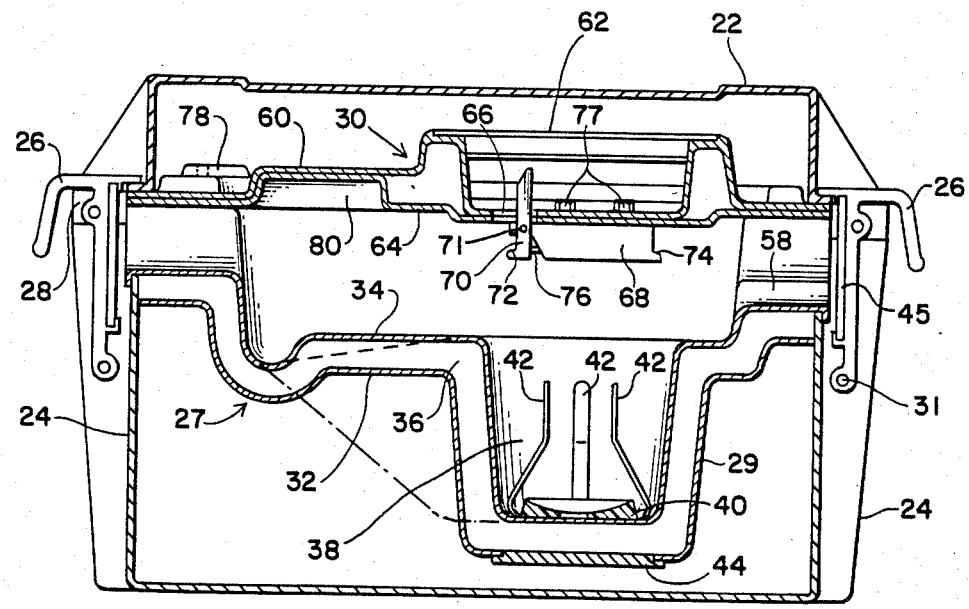
FIG. 2 is a front, sectional view of the shielding container in section.
Figure 4:
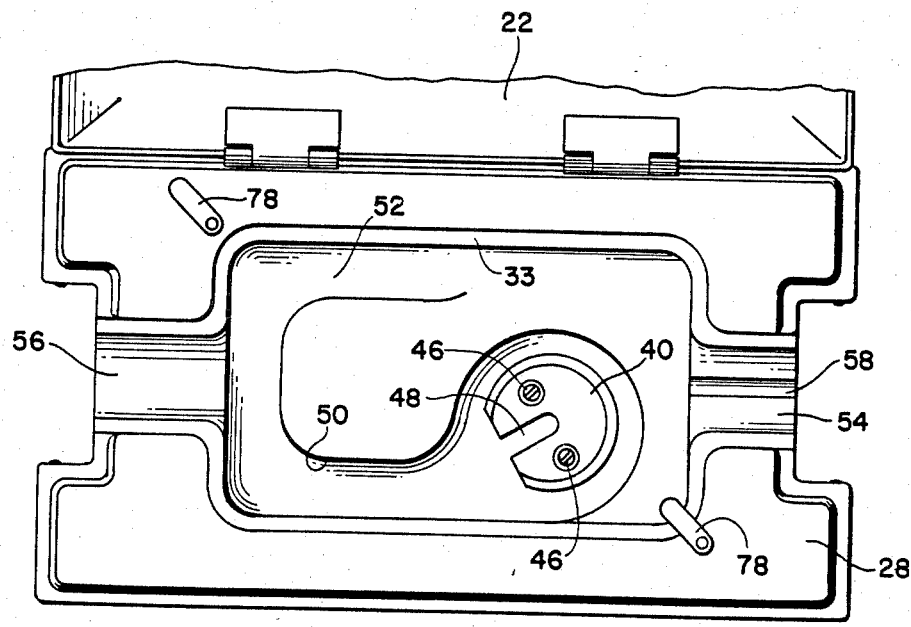
FIG. 4 is a top view of the shielding container with the lid removed illustrating the surface configuration of the inner shell of the container.
Figure 9:
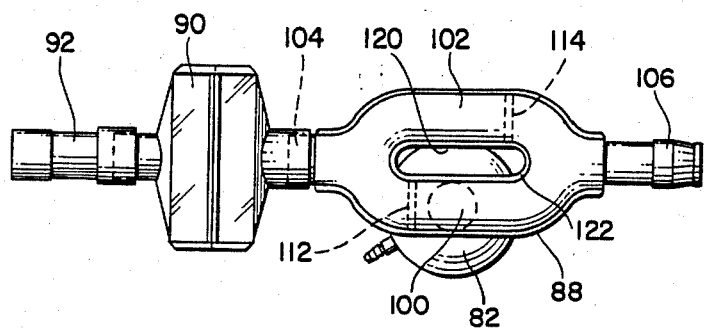
FIG. 9 is a top view of the manifold and nebulizer illustrated in FIG. 8.
Figure 8:
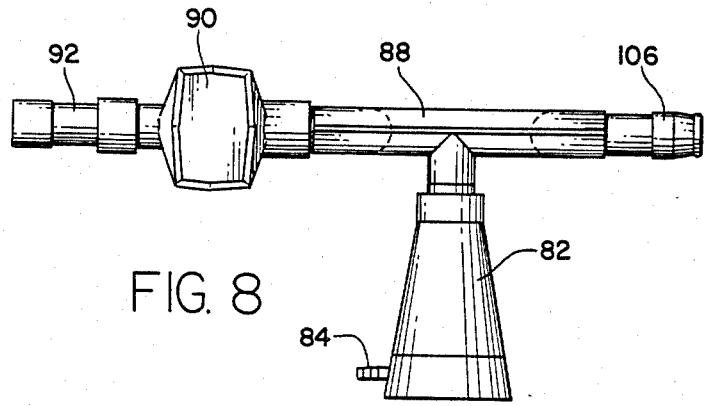
FIG. 8 is a side view of the manifold utilized to transport the radioaerosol and the nebulizer connected thereto.
Figure 10:
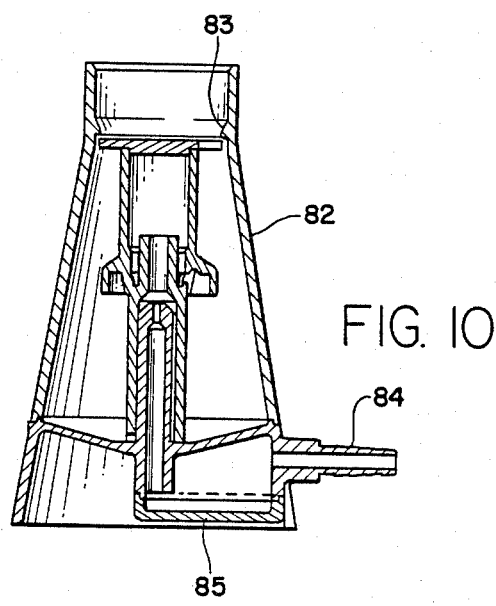
FIG. 10 is cross-sectional view of a nebulizer utilized with the invention.

As can best be seen in FIGS. 2 and 4, container 20 is provided with an inner shell 27 which is supported on and in outer shell 24. Inner shell 27 is formed with a top portion 28 which is adapted to be bonded to outer shell 24 around the periphery thereof. Inner shell 27 additionally has a lower portion 29 formed by outer wall 32 and inner wall 34. A cover shield 30, which will be described more fully hereinafter, is adapted to fit within the surfaces defined by inner wall 34 of the lower portion 29. Outer wall 32 and inner wall 34 define a channel 36 therebetween which can be filled with a suitable radiation shielding material (not shown) such as lead shot or the like. Inner wall 34 defines a nebulizer well 38 which generally conforms to the contours of the nebulizer 82 when it is located within well 38.

A support pad 40 is provided at the bottom of well 38 and secured thereto by means of screws 46 which can be seen most clearly in FIG. 4. A radial slot 48 is formed in the support pad 40 to accommodate the bottom portion 85 of nebulizer 82. Also provided in nebulizer well 38 are retaining spring elements 42 which are suitably formed from spring steel or the like and are adapted to contact the wall of nebulizer 82 to maintain it in a stable and upright position during use. Attached to the bottom of outer wall 32 is a plate 44 which is utilized to cover the opening through which lead shot or other suitable shielding material can be loaded into channel 36. Inner wall 34 is contoured and includes a ramp sidewall 50 which defines a ramp 52 extending about the periphery of inner wall 34 from the bottom of well 38 to the top of well 38 and eventually to groove 58 in the hemicylindrical surface 54 formed at one end of the inner shell 27. Ramp 52 is utilized to support a fluid delivery tube which extends from inlet port 84 on nebulizer 82 upwardly upon ramp 52 through groove 58 where it can be attached to a source of air or oxygen to drive nebulizer 82 in a conventional manner. Ramp 52 provides a convenient mechanism for ensuring that the fluid delivery tube 86 does not kink or become unduly twisted and thus prevent fluid delivery and operation of the nebulizer 82.

Handles 26 are hingedly connected at pivot points 31 to outer shell 24 and are adapted to engage lid 22 in the closed position. Only one hinge mechanism has been illustrated but it is understood that handle 26 on the other side of container 20 is connected in the same fashion. Handle 26 is additionally provided with radiation shielding material 45 in the form of a lead plate or the like.

Inner wall 34 also defines a support surface 33 about the periphery of inner shell 27 dimensioned to mate with cover shield 30, which is formed with the same design about its periphery. Cover shield 30 is formed with a contoured top plate 60 on which is mounted a handle 62. Attached to the bottom of top plate 60 is a contoured shield plate 64 which is made from radiation shielding material. Both top plate 60 and shield plate 64 are formed with a hole 66 extending therethrough to accommodate a movable latch 70 which is utilized to engage the manifold 88.

Movable latch 70 is pivotably attached to a latch support 68 at pivot point 71. Latch 70 is formed with a surface 72 and latch support 68 is formed with a surface 74 which are adapted to engage a portion of the manifold 88. Latch surface 72 is movable, whereas latch surface 74 remains fixed. A spring-loaded latch rod 76 is provided between latch 70 and latch support 68 in order to bias latch 70 to its engaged position. Latch rod 76 is conveniently located within a bore formed in latch support 68. Latch support 68 is conveniently attached to cover shield 30 by means of screws 77. Means to retain cover shield 30 are provided by means of pivotable arms 78 which are connected to the top portion 28 of inner shell 27 and adapted to be moved over the cover shield 30 when it is in position. The contours of the cover shield 30 define a filter well 80 which is adapted to accommodate filter 90 when it is in place as part of the transport means for the radioaerosol, as illustrated most clearly in FIG. 3.

Figure 3:
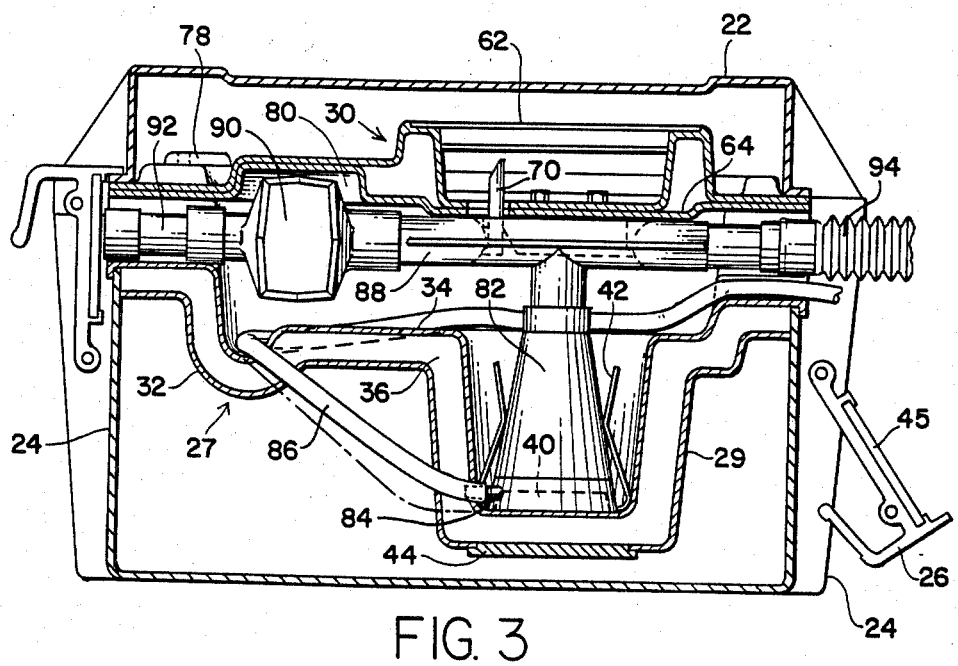
FIG. 3 is a front, sectional view of the shielding container including the radioaerosol source generator and transport means positioned within the container.

FIG. 3 illustrates generally the relative positions of the various components of the apparatus when the radioaerosol system is in use. As can be seen therein the nebulizer 82 is positioned on support pad 40 in well 38 and retained by spring members 42 in a stable and upright position. The lower end of the nebulizer 82 is provided with a connector 84 which is adapted to receive the end of a fluid supply tube 86 which is supported on ramp 52 and directed through the groove 58 formed in inner shell 27. Fluid supply tube 86 is connected to a source of air or oxygen to drive the nebulizer in a conventional manner. The top of nebulizer 82 is formed with a molded, inner ring 83 which is adapted to locate within a groove 118 on a connector 116 at the bottom of the manifold 88, as can be seen most clearly in FIG. 11. The nebulizer 82 is connected to the manifold via connector 116 and the manifold 88 is engaged by movable latch 70 and thus is secured to cover shield 30.

Figure 12:
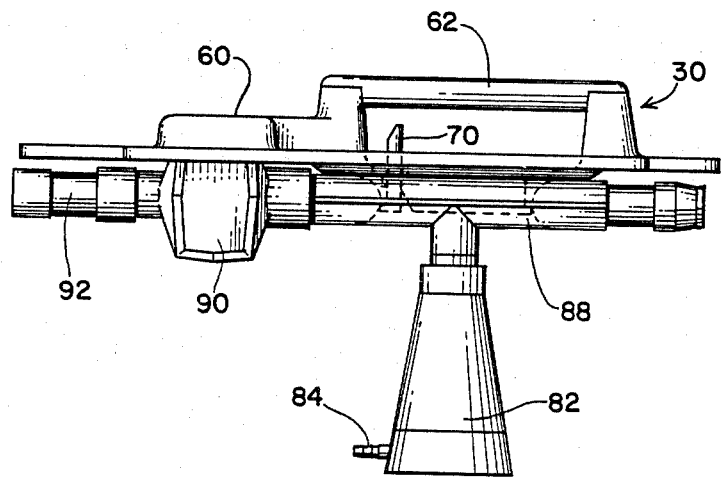
FIG. 12 is a side view of the cover shield portion of the shielding container with the transport means and the radioaerosol source generator connected.

End 104 of manifold 88 is connected to a biological filter 90 and the other end 106 of manifold 88 is connected to a patient breathing tube 94 which extends to the mouthpiece of the patient. An extension 92 is placed on the end of filter 90 to assist in the support of the transport means within the shielding container. When cover shield 30 is attached to manifold 88, as can best be seen in FIG. 12, cover shield 30 and the transport means (including manifold 88, filter 90 and filter extension 92) and the radioaerosol generating source, i.e., the nebulizer 82, can be removed from the shielding container as a unit. Thus, in removing that system as a unit from the shielding container, the operator still is protected by cover shield 30 in handling the manifold 88, filter 90 and nebulizer 82 and associated tubing which may be contaminated with radioactive material. The entire unit can then be placed over a suitable disposal container and when latch 70 is pivoted to release manifold 88, nebulizer 82, filter 90 and associated tubing also are released so that all of the contaminated components will be disposed of without unduly endangering an operator.

Figure 11:
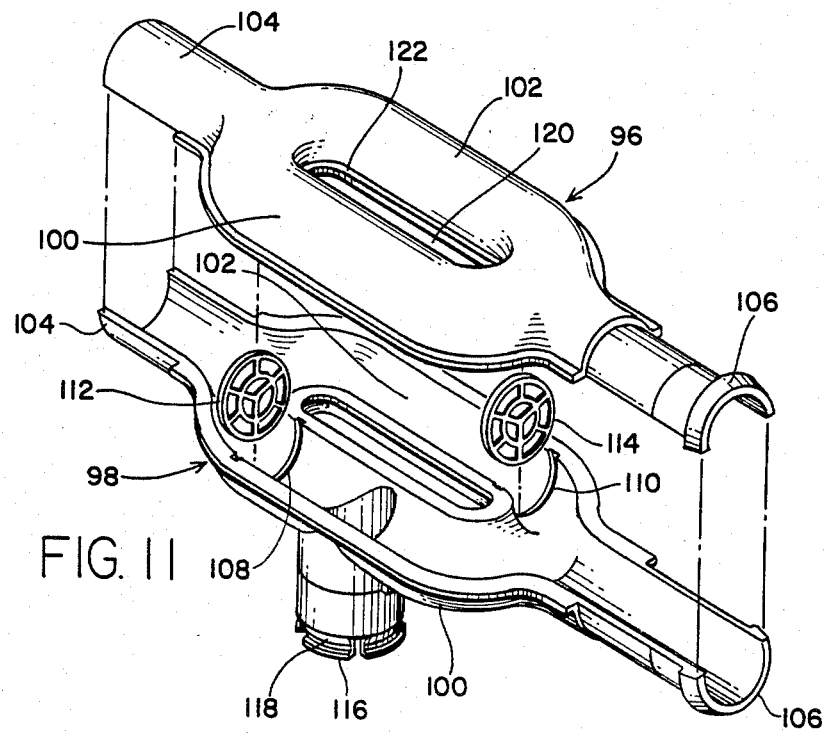
FIG. 11 is an exploded view of the manifold illustrating the component parts.

As can be seen most clearly in FIG. 11, the manifold 88 of this invention is formed with an upper section 96 and a lower section 98 which when joined together form an inlet conduit 100 and an outlet conduit 102 which join at one end to form a connector 104 which is adapted to connect to the filter 90 and at the other end form a connector 106 which is adapted to connect to the patient breathing tube 94. Inlet conduit 100 and outlet conduit 102 define an opening 120 which is provided with a lip extending outwardly from conduit 100 and 102 into the opening. The function of lip 122 is to be engaged by surfaces 72 and 74 on the latching mechanism. A one-way check valve 112 is situated in a groove 108 formed in inlet conduit 100 between connector 104 and connector 116. Valve 112 is conventional and can be of the diaphragm type. Valve 112 permits flow from the atmosphere through the filter from connector 104 in a direction toward connector 106 though inlet conduit 100. However, the one-way nature of valve 112 will prevent fluid flow in the reverse direction, for example when the patient exhales. In a similar manner, a one-way valve 114 is provided in a groove 110 in outlet conduit 102. One-way valve 114 can again be of the diaphragm type and will permit flow in a direction from connector 106 through outlet conduit 102 to connector 104. Valve 114 will, however, prevent flow in the opposite direction. As described above, latch support 68 and latch 70 are adapted to fit within opening 120 such that surfaces 72 and 74 can engage the lower portion of lip 122 formed on inlet conduit 100 and outlet conduit 102. While lip 122 extends entirely around the periphery of opening 120, it is understood that only portions thereof would have to be provided in order to attach manifold 88 to cover shield 30.

In the event it is not appropriate to dispose of the transport means and the nebulizer 82 immediately after use, the patient tube 94 and the fluid delivery tube 86 can be disconnected and handles 26 can be moved upwardly and latched to lid 22 to position radiation shielding material 45 over the ends of the openings in the outer shell at each side of the container. Thus the container 20 effectively isolates the radioactive material from the surrounding atmosphere and the radioactive material can be left within container 20 until such time as the level of radioactivity has been reduced to a point that the disposal is appropriate.

During operator use, lid 22 is elevated and an aerosol generator, such as nebulizer 82 is connected to the fluid delivery tube 86 and positioned within the bottom of well 38 upon support pad 40. Tube 86 is supported on ramp 52 and directed through groove 58. A radiolabeled solution such as 99 m technetium diethylenetriaminepentaacetate or sulphur colloid in a shielded syringe in a conventional manner is dispensed into nebulizer 82. Then the manifold 88 connected to cover shield 30 and the filter 90 and associated tubing are positioned above nebulizer 82 and inserted in the contour formed by inner wall 34 onto support surface 33. By pushing downwardly on cover shield 30, which is connected to manifold 88, connector 116 of manifold 88 is forced into the upper end of nebulizer 82 and groove 118 and ring 83 engage to secure the nebulizer 82 to manifold 88. The patient tubing 94 can than be attached to end 106 of manifold 88, unless it was attached beforehand.

After connection of fluid delivery tube 86 to a source of driving fluid for nebulizer 82, the inhalation process can proceed in a conventional manner. As the patient inhales, the patient breathes radiolabeled aerosol generated from nebulizer 82. In the event the fluid flow volume is insufficient to satisfy the inhalation volume requirement of the patient, additional air will be brought in from the atmosphere through filter extension 92, filter 90, valve 112 and through inlet conduit 100. In that manner the patient does not feel uncomfortable if the aerosol flow volume is too low to satisfy his demands. When the patient exhales, the expired gases pass through valve 114 and outlet conduit 102 where any radioactive substance is collected by filter 90. At the end of the procedure, the flow of drive fluid to the nebulizer is ended and the patient is disconnected from the unit. At that time the filter, manifold 88 and nebulizer 82 can be removed from the container 20 as a unit for immediate disposal or, as has been described previously, handles 26 can be pivoted upwardly to latch to lid 22 and close the end openings through which the fluid transport system communicated with the atmosphere and the patient.

While the invention has been described with reference to the specific embodiments thereof, it should be understood by those skilled in the art that various changes can be made and equivalents may be substituted therefore without departing from the true spirit and scope of the invention. All such modifications are intended to be within the scope of the claims appended here too.

What is claimed is:

1. A manifold comprising a first, rigid, tubular conduit and a second, rigid, tubular conduit joined at one end to form a first tubular connector and at the other end to form a second tubular connector, said first and second conduits being spaced from each other to define an opening therebetween;
   a third tubular connector located in said first conduit between said first and second connectors;
   attachment means formed on at least one of said first and second conduits and associated with said opening to attach said manifold to a support means;
   a first, one-way valve located in said first conduit between said first connector and said third connector permitting fluid flow through said first conduit in a direction from said first connector toward said second connector and preventing fluid flow in the reverse direction; and
   a second, one-way valve located in said second conduit permitting fluid flow through said second conduit in a direction from said second connector toward said first connector and preventing fluid flow in the reverse direction.

2. The manifold of claim 1 wherein said attachment means includes a lip formed on at least a portion of said one of said conduits and said lip extends into said opening.

3. The manifold of claim 2 wherein said third connector has means thereon for rigidly securing said third connector to a fluid source.

4. The manifold of claim 3 wherein said securement means is a groove formed on the outer circumference of said third connector.

* * * * *